(12) United States Patent
Trunin et al.

(10) Patent No.: US 8,933,271 B2
(45) Date of Patent: Jan. 13, 2015

(54) METHOD FOR PREPARING AMMONIUM SALTS OF FUMARIC OR SUCCINIC ACID

(75) Inventors: Roman Anatolievich Trunin, Moscow (RU); Mikhail Lvovich Uchitel, Mytishi (RU); Evgenij Iljich Maevskij, Pushino (RU); Vladimir Izrailevich Heifets, Tula (RU); Svetlana Yakovlevna Chernitzkaya, legal representative, St. Petersburg (RU); Donna Kasseinova, Palos Verdes Estates, CA (US); Galina Nikolaevna Ermakova, Tula (RU)

(73) Assignee: Lunada Biomedical, LLC, Los Angeles, CA (US)

( * ) Notice: Subject to any disclaimer, the term of this patent is extended or adjusted under 35 U.S.C. 154(b) by 991 days.

(21) Appl. No.: 13/061,148

(22) PCT Filed: Aug. 24, 2009

(86) PCT No.: PCT/RU2009/000428
§ 371 (c)(1),
(2), (4) Date: Jan. 17, 2012

(87) PCT Pub. No.: WO2010/041978
PCT Pub. Date: Apr. 15, 2010

(65) Prior Publication Data
US 2012/0130125 A1 May 24, 2012

(30) Foreign Application Priority Data

Aug. 28, 2008 (RU) .................................. 2008134833

(51) Int. Cl.
*C07C 51/43* (2006.01)
*C07C 51/41* (2006.01)

(52) U.S. Cl.
CPC ............... *C07C 51/43* (2013.01); *C07C 51/412* (2013.01)
USPC .......................................................... 562/590

(58) Field of Classification Search
USPC ......................................................... 562/590
See application file for complete search history.

*Primary Examiner* — Shawquia Jackson
(74) *Attorney, Agent, or Firm* — Bardmesser Law Group

(57) ABSTRACT

An improved process for preparing ammonium salts from fumaric or succinic acid, is described. The method consists of neutralizing the corresponding acid carbonate or ammonium bicarbonate at a molar stoichiometric or greater than the stoichiometric ratio of 4-5% in a saturated aqueous solution of the synthesized salt at a temperature not exceeding 40° C., followed by separation of the product and drying at a temperature not exceeding 70° C. After separation of the ammonium salts, the filtrate can be re-used. Isolation of the product is usually carried out by cooling the reaction mixture to a temperature of 15-18 C.°. The product comes out in almost crystalline form. Saturated aqueous solution of the synthesized salt is formed by the interaction of carbonate or ammonium bicarbonate with the appropriate acid at a temperature not exceeding 40° C. It is possible to obtain cleaner salt concentration weighing more than 99% and not yielding lower than 98%. The method allows for an increase in the yield of targeted products and ensures their consistent high quality due to their formation in crystalline form.

13 Claims, No Drawings

METHOD FOR PREPARING AMMONIUM SALTS OF FUMARIC OR SUCCINIC ACID

CROSS-REFERENCE TO RELATED APPLICATION

This Application is a National Phase of PCT/RU2009/000428, filed on Aug. 24, 2009, which claims priority to RU 2008134833, filed on Aug. 28, 2009, which are incorporated by reference herein in their entirety.

FIELD OF THE INVENTION

The invention is related to a method for obtaining mono- and di-ammonium salts from fumaric (FA) or succinic (SA) acids, and, in particular, to methods for industrial production of such salts, which are generally used in manufacturing biologically active substances or medicine, as well as in the veterinary and food industries.

BACKGROUND OF THE RELATED ART

Despite the long history of its use (ammonium succinate was known as the anticonvulsant medication of the 19th century, see H. O. Hager, Guide to Pharmaceutical and Medical-chemical Practice, Saint Petersburg, 1889, table 1, pp. 164-167), ammonium salt from fumaric and succinic acid is not available on an industrial scale ("Succinic Acid in Medicine, the Food Industry, and Agriculture", M. N. Kondrashova et al., ed., Pushchino, 1996, p. 262). This article points out previously, ammonium succinate was used as a chemical reagent in the USSR at the Yerevan chemical factory and for the GDL at the VEB Laborchemie Apolda enterprise.

There are several known methods of obtaining preparative ammonium salts from these acids, such as the method for producing di-ammonium fumarate from fumaric acid and ammonia in a hot alcoholic solution described in the "Beil" handbook, table 2, suppl. 1, page 301.

The disadvantage of implementing this method on an industrial scale is the use of volatile solvents and ammonia gas, which has a safety limit of release for equipment working under pressure and requires power expenditure and cooling agents for the regeneration of the solvent.

A method of obtaining salts from succinic acid by hydrogenation of maleic acid salts in the presence of a palladium-nickel catalyst is described in RU Patent No. 2129540. According to this method, ammonium succinate is obtained from maleic anhydride and 24% aqueous ammonia as a result of hydrogenation of the formed di-ammonium salt of the maleic acid under hydrogen pressure of 15 atm at 80° C. in the course of 5 hours using a palladium-nickel catalyst.

The disadvantage of such a method is the use of expensive catalysts, pressurized equipment, and hydrogen, which calls for a huge expenditures for safety measures.

It is also known that one can obtain ammonium succinate of carboxylic acids, free from high yielding halogens, as well as the interaction of quarternary ammonium salts with acid metal salt in a mixture of water and alcohol with the distilled solvent (see JP2002-179614 and JP57-050937).

It is known that one can obtain ammonium and/or acid metal salt from di- and tricarboxylic acids for photographic processes of the reactions di or tricarboxylic acids or their anhydrides with ammonium and/or metal salt bicarbonate in the solid phase with the temperature of 40-100 C.° using polymers (see EP1284254A1).

Also, neutralization of oxalic acid, ammonium carbonate, by mixing these components in the equivalent parts of distilled water when exposed with mixing and filtering with a dried paste, is described in Alt-Photo-Process-L:Re:Sodium chloropalladite, www.usak.ca/lists/alt-photo-process/2004/jan04/0295.htm (January 2004). This method, in certain aspects, is similar to the proposed method for obtaining ammonium salts from dicarboxylic acids. However, there is no data on the quality of the output of the product obtained and the parameters of the division and drying. This method may only be used in laboratories.

A method is the method for producing an aqueous solution di-ammonium salt of succinic acid for the synthesis of succinimide is described by H. Clark and L. Berg (Synthesis of organic preparation, sb. 2, edition BLETT, foreign literature, M, 1949, c. 439). The method includes the following stages:

236 grams (2 mall) of succinic acid is placed In a 1 liter Wurtz flask with a side outlet 236, and during cooling and shaking, 270 ml (243, 4 Mol) 28% aqueous ammonia specific weight (0.90) is slowly poured. With that, most of the acid dissolves, forming a clear solution of di-ammonium salt. The solution is subjected to distillation and decomposition to yield succinimide as a result of salt decomposition. However, there is no data in this publication showing the temperature of the reaction, the rate at which ammonia solution was added, the method of salt extraction, the parameters of salt drying, or the quality of the obtained di-ammonium salt from succinic acid.

The Clark et al. reference does not contain any information concerning the reaction temperature range, rate of introduction of aqueous ammonia, salt extraction method, salt drying mode, quality of the resulting di-ammonium salt of the succinic acid. The thermal instability of ammonium succinate (see R.J.Chem. 1989, 4Б 3110 [WHAT?]; Thermochim. acta—1988-132.—pp. 229-233 Engl.) which dissociates at 360° K or 87° C., requires performance of a multistage vacuum drying for the salt production from its aqueous solution. In the process of producing salt from succinic acid and a 20-28% aqueous solution of ammonia, the resulting salt is in the form of a ~45% aqueous solution at 0°. In order for separation to occur there must be a multi-stage steaming of the salt under a vacuum because with a temperature of over 80° C., there is a possibility of the formation of succinimide accompanied by resinification. As a result of this separation, the salt takes on a beige tint. In addition, the organization and maintenance of an evaporation plant requires a large expenditure of energy and coolants. In the description of the method, there is no evidence about the yield of the salt products. Therefore, this well-known method for obtaining ammonium succinate is meant solely for laboratory usage.

The object of the proposed method is to come up with a more adequate means for obtaining ammonium salt (mass no more than 99% and yield under 98%) from succinic and fumaric acids in a "green" manner for industrial production. This would increase the yield of target products and ensure their consistent high quality.

The object is achieved by obtaining ammonium salts from fumaric or succinic acid by neutralizing the corresponding acid-neutralizing compound in an aqueous medium. The difference between this method and the conventional one is the use of a neutralizing compound carbonate or ammonium bicarbonate at a molar stoichiometry or stoichiometry greater than a 4-5% ratio of acid and carbonate or ammonium bicarbonate, and performing neutralization in a saturated aqueous solution of the synthesized salt at a temperature not exceeding 40° C., followed by separation of the product and drying at a temperature not exceeding 70° C. The filtrate can then be recycled after the separation of the ammonium salts.

Isolation of the product is usually carried out by cooling the reaction mixture to a temperature of 15-18° C., with the product coming out in a predominantly crystalline form.

Saturated aqueous solution of the synthesized salt is prepared interaction carbonate or ammonium bicarbonate with the appropriate acid at a temperature not exceeding 40° C.

A more detailed process is described below:

(1) Mono-ammonium salt (fumarate or succinate) is derived from carbonate or ammonium bicarbonate and the corresponding acid in a molar ratio, respectively, 0.52/0.05:1 or 1.4/1:1;

(2) Di-ammonium salt (fumarate or succinate) is derived from carbonate or ammonium bicarbonate and the corresponding acid in a molar ratio, respectively, 4.1/4:1 or 2.1/2:1;

(3) Neutralization is brought to saturated form with a temperature of 18-20° C. solution of the synthesized salt;

(4) The optimal temperature of neutralization is 40° C.;

(5) The optimum dosage of succinic or fumaric acid (or ammonium carbonate and bicarbonate) is determined by the volume of foam above the level of suspension in the reactor (less than ⅓ of suspension) and lasts no more than 2 hours;

(6) Optimal time of exposure after dosing—1-2.5 hours at a temperature of 40° C. and depends on the device (the greater the volume, the greater the exposure);

(7) Final crystallization of sediment is carried to a temperature of 18-15°;

(8) Temperature for the sediment to dry is less than 70° C.;

(9) Ammonium bicarbonate is the preferred neutralizing agent, since it has a higher temperature of decomposition in comparison with ammonium carbonate;

(10) The filtrate is returned for recycling.

The proposed method can be broken down into the following:

With a temperature up to 40° C., in a saturated solution of synthesized salt (at 18-20° C.), carboxylic ammonium salt is charged and given dicarbonate acid in synthesis (upon formation of mono-ammonium salt bicarbonate or ammonium carbonate, carbonic acid is dosed in suspension) in the course of 2 hours, followed by exposure for 1-2.5 hours at a temperature not exceeding 40° C. and cooling the suspension to a temperature of 15-18° C. The precipitate is filtered on a vacuum filter and dried at a temperature not exceeding 70° C. until the smell of ammonia has subsided. The filtrate is then recycled. Targeted salt is obtained with a yield of 98-100%, containing molecules with a mass not exceeding 99%. The products fulfill the requirement of biologically active food additives containing harmful dyes, including

| | |
|---|---|
| Mass fraction of lead (Pb), % not more than | $5.0 \cdot 10^{-4}$ |
| Mass fraction of arsenic (As), % not more than | $3.0 \cdot 10^{-4}$ |
| Mass fraction of cadmium (Cd), % not more than | $1.0 \cdot 10^{-4}$ |
| Mass fraction of mercury (Hg), % not more than | $1.0 \cdot 10^{-4}$ |

IR spectroscopy confirmed the structure of salt and set them a high degree of purity. The assignment of bands in the infrared spectra of the main structural elements is held in accordance with the published data (L. Bellami, Infra-red spectrums of complex molecules, M., IL, 1963, p. 592; K. Nakanisi, Infrared Spectrums and the Formation of Organic Compounds, M., Mir, 1985, p. 216).

The invention is further illustrated by the following examples:

EXAMPLE NO. 1

Synthesis of Di-Ammonium Salt from Fumaric Acid ($C_4H_{10}N_2O_4$)

The reaction takes place in a saturated salt aqueous solution. To do this, 13.91 M (91.9 kg) or 7 M bicarbonate (0.672 kg) of ammonium carbonate is added to 3.43 liters of water and dosed 6.72 M (0.78 kg) of fumaric acid, preventing the rise of foam in the reactor of more than ⅓ of the original volume of the reaction mass. This yields 4.7 kg (about 4 liters), that is, 21% of the di-ammonium fumarate solution. The obtained solution is then charged with 19.46 M (1.54 kg) of bicarbonate or 10 M (0.960 kg) of ammonium carbonate, and with a temperature of no more than 40° C., in the course of 2 hours 9.73 M (1.129 kg) of fumaric acid is dosed. The reaction goes on with heat absorption and release of carbon dioxide. That is why the reaction mixture is heated.

The reaction occurs with heat absorption and release of carbon dioxide, so the reaction mixture is heated (optimum temperature 40° C.) and does not allow the foam to rise by more than ⅓ of the initial reaction volume. After the dosage of fumaric acid at a temperature of 40° C., the shutter speeds for one hour, after which the mixture is cooled to a temperature of 15-18° C. The result is 1.6 kg of wet crystalline precipitate and 4.7 kg of filtrate. The filtrate is returned for reuse, and the precipitate is dried at a temperature not exceeding 70° C. When dried, the result is 1.36 kg of ammonium fumarate, containing mostly a 99% mass and 98% water. The salt yield is 99%.

Contents of harmful dyes:

| | |
|---|---|
| Mass fraction of lead (Pb), % not more than | $4.5 \cdot 10^{-4}$ |
| Mass fraction of arsenic (As), % not more than | $2.5 \cdot 10^{-4}$ |
| Mass fraction of cadmium (Cd), % not more than | $0.7 \cdot 10^{-4}$ |
| Mass fraction of mercury (Hg), % not more than | Not detected |

EXAMPLE NO. 2

Synthesis of Di-Ammonium Salt from Succinic Acid ($S_4H_{12}N_2O_4$)

Initially, an operation is performed for the preparation of saturated salt solution from succinic acid. The reactor is charged with a volume of 1 m³ of water, which is mixed and then loaded with 129.6 kg (1640.5 M) ammonium bicarbonate, while simultaneously heating the reaction mixture with steam to a temperature of 40-38° C. The dosage of succinic acid (96 kg or 813.56 M) is kept at a temperature of 32-38° C. for 2 hours. The extract of the reactive mass cools to 16° C. and is filtered on a Nutsche filter. This yields 191.4 k of wet sediment, almost entirely in crystalline form and 180 liters of filtrate, which is used in the following salt synthesis operation. The wet sediment dries at a temperature of 50-70° C. until the smell of ammonia disappears, which yields 145 kg of dry sediment containing molecules at 100% mass.

The salt yield is 98%.

Contents of harmful dyes:

| | |
|---|---|
| Mass fraction of lead (Pb), % not more than | $4.5 \cdot 10^{-4}$ |
| Mass fraction of arsenic (As), % not more than | $2.0 \cdot 10^{-4}$ |
| Mass fraction of cadmium (Cd), % not more than | $0.5 \cdot 10^{-4}$ |
| Mass fraction of mercury (Hg), % not more than | $0.3 \cdot 10^{-4}$ |

IR spectroscopy showed an absence of the salt bands characteristic of succinic acid (1310 and 1200 cm) and ammonium bicarbonate (700 cm), which shows a high purity of salt.

EXAMPLE NO. 4

Synthesis of Di-Ammonium Salt from Succinic Acid ($S_4H_{12}N_2O_4$)

The synthesis is carried out in about in the same conditions as in example 3, however, instead of a freshly saturated solution of salt, a recycled (180 L) of filtrate is used, generating 148 kg of ammonium succinate with a content mass of 99.8%. Salt yield is 100%.

EXAMPLE NO. 5

Synthesis of Mono-Ammonium Salt from Succinic Acid ($C_4H_{12}N_2O_4$)

Initially, 2 liters of a saturated solution of salt water is prepared by taking 1 liter of water, 0.65 kg (8.23 M) of ammonium bicarbonate and mixing in 0.971 kg (8.23 M) of succinic acid at a temperature of 38 to 40° C. At a temperature of 38° C. 1.157 kg (9.81 M of succinic acid is added to the resulting solution and 0.775 kg (9.81 M) of ammonium bicarbonate is dispensed for one hour then cooled to 16° C. and filtered on a Nutsche filter cake, which is dried at 70° C. The filtrate is then returned for recycling. This yields 1.3 kg of mono-ammonium salt containing a 99.5% mass. The salt yields at 98.5%.

It should also be appreciated that various modifications, adaptations and alternative embodiments thereof may be made within the scope and spirit of the present invention. The invention is further defined by the following claims.

What is claimed is:

1. A method for preparing ammonium salts of fumaric acid, comprising:
   neutralizing the fumaric acid with a neutralizing compound in an aqueous medium;
   wherein the neutralizing compounds is at least one of ammonium carbonate and bicarbonate in a molar stoichiometric solution;
   the neutralization is performed in a saturated aqueous solution of the ammonium salt at the temperature not exceeding 40° C.,
   separating the ammonium salt from the aqueous solution; and
   drying the ammonium salt at a temperature not exceeding 70° C.

2. The method of claim 1, wherein the saturated aqueous solution of the synthesized salt is prepared by a reaction between ammonium carbonate or bicarbonate and the fumaric acid at a temperature not exceeding 40° C.

3. The method of claim 2, wherein the separation is carried out by cooling the reaction mixture to the temperature of 15-18 degrees C. and separating the resulting precipitate as crystals.

4. The method of claim 3, wherein a filtrate resulting from the separating step is recycled after the separating.

5. A method for preparing ammonium salts of succinic acid, comprising:
   neutralizing the succinic acid with a neutralizing compound in an aqueous medium;
   wherein the neutralizing compounds is at least one of ammonium carbonate and bicarbonate in a molar stoichiometric solution;
   the neutralization is performed in a saturated aqueous solution of the ammonium salt at the temperature not exceeding 40° C.,
   separating the ammonium salt from the aqueous solution; and
   drying the ammonium salt at a temperature not exceeding 70° C.

6. The method of claim 5, wherein the saturated aqueous solution of the synthesized salt is prepared by a reaction between ammonium carbonate or bicarbonate and the succinic acid at a temperature not exceeding 40° C.

7. The method of claim 6, wherein the separation is carried out by cooling the reaction mixture to the temperature of 15-18 degrees C. and separating the resulting precipitate as crystals.

8. The method of claim 7, wherein a filtrate resulting from the separating step is recycled after the separating.

9. A method for preparing ammonium salts of fumaric acid, comprising:
   neutralizing the fumaric acid with a neutralizing compound in an aqueous medium;
   wherein the neutralizing compound is a mixture of fumaric acid and one of carbonate or bicarbonate ammonium, with a ratio between the acid and the carbonate or bicarbonate ammonium exceeding the stoichiometry by 4-5%;
   the neutralization is performed in a saturated aqueous solution of the ammonium salt at the temperature not exceeding 40° C.,
   separating the ammonium salt from the aqueous solution; and
   drying the ammonium salt at a temperature not exceeding 70° C.

10. The method of claim 9, wherein the saturated aqueous solution of the synthesized salt is prepared by a reaction between ammonium carbonate or bicarbonate and the fumaric acid at a temperature not exceeding 40° C.

11. The method of claim 10, wherein the separation is carried out by cooling the reaction mixture to the temperature of 15-18 degrees C. and separating the resulting precipitate as crystals.

12. The method of claim 11, wherein a filtrate resulting from the separating step is recycled after the separating.

13. A method for preparing ammonium salts of succinic acid, comprising:
   neutralizing the succinic acid with a neutralizing compound in an aqueous medium;
   wherein the neutralizing compound is a mixture of succinic acid and one of carbonate or bicarbonate ammonium, with a ratio between the acid and the carbonate or bicarbonate ammonium exceeding the stoichiometry by 4-5%;
   the neutralization is performed in a saturated aqueous solution of the ammonium salt at the temperature not exceeding 40° C.,
   separating the ammonium salt from the aqueous solution; and
   drying the ammonium salt at a temperature not exceeding 70° C.

* * * * *